United States Patent [19]

Harris

[11] Patent Number: 5,449,341
[45] Date of Patent: Sep. 12, 1995

[54] COMPRESSION SUPPORT BRACES

[75] Inventor: Alvin R. Harris, Hackensack, N.J.

[73] Assignee: Becton, Dickinson and Company, Franklin Lakes, N.J.

[21] Appl. No.: 106,682

[22] Filed: Aug. 16, 1993

[51] Int. Cl.$^6$ .................... A61F 13/00; A61F 15/00
[52] U.S. Cl. ........................... 602/63; 602/75; 602/14; 2/16
[58] Field of Search .............. 602/60, 61, 62, 63, 602/75, 76, 59, 14, 26; 2/16, 22

[56] References Cited

U.S. PATENT DOCUMENTS

| | | | |
|---|---|---|---|
| 4,084,586 | 4/1978 | Hettick | 128/157 |
| 4,426,414 | 1/1984 | Wilkerson | 428/102 |
| 4,534,354 | 8/1985 | Bonner, Jr. et al. | 602/75 |
| 4,832,010 | 4/1989 | Lerman | 128/165 |
| 4,961,418 | 10/1990 | McLaurin-Smith | 602/63 |

OTHER PUBLICATIONS

American Heritage Dictionary, Second College Edition, (1982), p. 1256.

*Primary Examiner*—Paul B. Prebilic
*Attorney, Agent, or Firm*—Arthur D. Dawson

[57] ABSTRACT

A multisection composite material useful in forming compression braces for orthopedic support of a body part includes a user contacting fabric section, an outermost fabric section formed from bonding two dissimilar fabrics and an intermediate section formed from a closed cell foam. The user contacting fabric section is a fabric having multidimensional stretch properties formed from hydrophobic fibers and bonded to a surface of the intermediate foam section. The outermost section includes a first fabric layer having multidimensional stretch properties formed from hydrophilic fibers and a second fabric layer having multidimensional stretch properties formed from hydrophobic fibers. The intermediate foam section has a first surface and a second surface and a multiplicity of perforations therethrough from the first surface to the second surface. The foam has multidimensional elastic properties sufficient for providing compressive strain useful for supporting the body part. The first layer of the outermost section is bonded to the second surface of the intermediate section. The composite material has a direction of minimum stretch and a direction of maximum stretch. Moisture emitted from a user's skin passes through the hydrophobic user contacting section to the intermediate section whereupon it passes through the perforations and is spread by the hydrophilic first fabric layer. The invention includes compressive orthopedic support braces for the wrist, elbow, thigh, knee and ankle formed from the material of the invention in sizes suitable for users having different physical stature. A method for making braces with substantial uniformity of compressive support of the present invention includes identifying the direction of maximum stretch required in the design and cutting it to shape in alignment with the direction of maximum stretch in the material.

2 Claims, 4 Drawing Sheets

COMPRESSION SUPPORT BRACES

FIELD OF THE INVENTION

This invention relates to a composite material useful for forming compression braces for orthopedic support of a body part. More particularly, the invention relates to braces formed of the composite having improved capability to pass moisture emitted from the user's skin covered by the brace and a method for making braces.

BACKGROUND OF THE INVENTION

There are many forms of compressive supports available for body parts. Historically, people with a need to provide additional support to wrists, elbows, thighs, knees and ankles used strips of cloth to wrap and support the body part. These early wraps evolved into formed braces, often including both cloth and leather and having laces to vary the compression. With the development of elastics, wraps were elasticized and evolved into specialized knit braces which incorporated the elastic into a knit structure. Many current commercial products are available using elasticized knit structures.

More recently laminated foam materials, originally developed for wet suits used in diving, were formed into compression braces for body parts. A U.S. Pat. No. 4,084,586 to Hettick teaches a variety of support devices formed from closed cell neoprene foam laminated on both sides with a thin nylon fabric. While braces prepared according to the teachings of the Hettick patent provided good support and retained warmth, they also retained moisture emitted from the skin of the user causing the user's skin covered by the brace to become saturated with moisture.

U.S. Pat. No. 4,832,010 to Lerman provided a partial solution to the retained moisture problem. The Lerman patent teaches braces formed from a closed cell neoprene foam having a stretchable porous fabric laminated to both sides of the foam. However, to address the retained moisture problem, the Lerman patent further teaches providing a multiplicity of relatively large air holes extending through and dispersed across the surface of material. The Lerman patent teachings suggest that, to maintain the compressive properties of the foam, the holes be limited to between about three and ten percent of the surface of the brace.

While a brace according to the Lerman patent provides some relief to the accumulated moisture problem seen when orthopedic braces are formed from closed cell foam, there is still a need for increasing the transport of emitted skin moisture out of an orthopedic brace and away from the skin where the brace is formed using a closed cell foam as a support component.

SUMMARY

A multisection composite material useful in forming compression braces for orthopedic support of a body part includes a user contacting fabric section, an outermost fabric section and an intermediate section formed from a closed cell foam. The user contacting fabric section is formed from substantially hydrophobic fibers having multidimensional stretch properties. The outermost fabric section is formed from bonding two dissimilar fabrics. These dissimilar fabrics include a first fabric layer having multidimensional stretch properties and formed from hydrophilic fibers. A second fabric layer of the outermost section formed from hydrophobic fibers has multidimensional stretch properties. The intermediate section, which is formed from closed cell foam, has a first surface and a second surface with a multiplicity of perforations therethrough from the first surface to the second surface. The intermediate layer has multidimensional elastic properties which are sufficient to provide compressive strain useful for support of the body part. The intermediate section first surface is bonded to a surface of the user contacting section and the second surface is bonded to the first fabric layer of the outermost section.

Desirably the user contacting section in the preferred embodiment of the present invention is a fabric formed from a hydrophobic fiber such as, but not limited to nylon, polyester, polypropylene, blends thereof and the like. Preferably the user contacting section fabric is a longitudinally slit circular knit fabric formed from nylon, providing the fabric with a longitudinal direction of minimum stretch and an orthogonal direction of maximum stretch.

The outermost section may include a first fabric layer made from hydrophilic fibers such as cotton, wool, silk, viscose rayon, blends of cotton, wool, silk, viscose rayon and the like. The second fabric layer is bonded to the first fabric layer and desirably is made from hydrophobic fibers such as nylon, polyester, polypropylene, and blends of nylon, polyester, polypropylene and the like. Preferably the first fabric layer is a circular knit formed from cotton fibers and the second fabric layer is a circular knit formed from nylon. Preferably the first and second fabric layers are bonded together by overlapping yarns or fibers of the first fabric layer and the second fabric layer as a common circular knit. The preferred outermost segment is longitudinally slit from the circular knit providing the outermost segment with a longitudinal direction of minimum stretch and an orthogonal direction of maximum stretch. Preferably the composite material of the present invention is formed by bonding the user contacting segment and the outermost segment to the intermediate foam layer with the directions of maximum stretch aligned.

A compression brace for a body part of the present invention includes a substantially tubular structure having a passageway therethrough and open from a first end to a second end. The tubular structure preferably is formed from a multisection composite material having a user contacting fabric section, an outermost fabric section and an intermediate section formed from a closed cell foam.

The user contacting fabric section is formed from substantially hydrophobic fibers, preferably a longitudinally slit circular knit nylon which has multidimensional stretch properties with a longitudinal direction of minimum stretch and an orthogonal direction of maximum stretch.

The outermost fabric section is formed from bonding two dissimilar fabrics. The dissimilar fabrics include a first fabric layer formed from hydrophilic fibers and a second fabric layer formed from hydrophobic fibers. Preferably, the first fabric layer is formed from a circular knit cotton and has multidimensional stretch properties with the second fabric layer formed from a circular knit nylon also having multidimensional stretch properties. Preferably, the first fabric layer is bonded to the second fabric layer by linkage of overlapping fibers and yarns from the first layer and the second layer in a common circular knit which is longitudinally slit. The preferred outermost section has a longitudinal direction of minimum stretch and an orthogonal direction of maximum stretch.

The intermediate foam section has a first surface and a second surface with a multiplicity of perforations therethrough from the first surface to the second surface. The intermediate foam section has multidimensional elastic properties sufficient to provide compressive strain useful for support of the body part. The intermediate section first surface is bonded to a surface of the user contacting section, with the second surface being bonded to the first fabric layer of the outermost section so that the second fabric layer forms the outside surface of the brace. Preferably the user contacting segment and the outermost segment are bonded to the intermediate foam layer with the directions of maximum stretch aligned.

The composite material is formed into a compression brace by cutting a sheet of the material to at least one shape having edges to be joined to form a substantially tubular structure. A design for the shape is determined by the intended application of the brace, i.e. the wrist, elbow, thigh, knee and ankle as well as the user's physical stature. Preferably when the design for the cut shape is laid out on the sheet to be cut to a shape, the directions of maximum and minimum stretch are considered so that the brace formed as the substantially tubular structure will provide substantially uniform compressive strain when applied to a properly sized body part.

A method of the present invention for making orthopedic support braces from the composite material of the present invention having a substantially uniform support profile for an individual brace and for substantially all of a production lot of braces includes selecting a series of size ranges suitable for a particular application. A design is developed for cutting a shape or shapes, which when joined at edges form a substantially tubular structure for supporting a body part. As part of the design process, the direction of the design that requires the maximum stretch is identified. The design is then placed on a sheet of the composite material of the present invention so that the identified direction of required maximum stretch is aligned with the direction of maximum stretch of the sheet. The sheet is then cut to the shape of the design and joined at the edges to form the substantially tubular brace structure. In manufacturing a production lot of braces of the present invention for a particular application, placement of the design on the composite sheet so that the direction of required maximum stretch for each unit of each shape to be cut is substantially aligned to the direction of maximum stretch for the sheet ensures substantial uniformity of the support profile for substantially all of the lot.

When the compression brace is worn by a user to provide support to a body part, moisture is emitted from the user's skin and, if the brace is impermeable, the moisture is trapped between the brace and the skin surface. The moisture problem is exacerbated by the fact that the amount of moisture emitted from the skin generally increases during exercise. A partial solution to the problem of entrapped moisture may be provided by perforations through the closed cell foam. However, since the perforations can only occupy a small percentage of the surface of the foam without reducing the ability of the foam to provide compressive strain necessary for support, considerable moisture is still entrapped.

In the present invention, moisture emitted from the user's skin is passed through the hydrophobic user contacting layer to the intermediate foam layer, whereupon it may pass through the multiplicity of perforations to the outermost layer. The outermost layer, by having a first hydrophilic layer bonded to the second surface of the foam, draws emitted moisture away from the perforations at the second surface of the foam and spreads it for evaporation through the second hydrophobic fabric layer. By drawing the emitted moisture away from the perforations and spreading it through the hydrophilic layer, the development of wet spots at the perforation openings is avoided. Additionally, the rate of evaporation, which is dependent on the surface area of the water, is substantially increased, and the rate of emitted moisture transport through the perforations is substantially enhanced, keeping the skin substantially dry. The enhanced moisture transport allows a user of a closed cell foam support brace the benefits of the support provided by the closed cell foam with increased comfort.

DETAILED DESCRIPTION

While this invention is satisfied by embodiments in many different forms, there will be described herein in detail preferred embodiments of the invention, with the understanding that the present disclosure is to be considered as exemplary of the principles of the invention and is not intended to limit the invention to the embodiments described. The scope of the invention will be measured by the appended claims and their equivalents.

Figure 1:
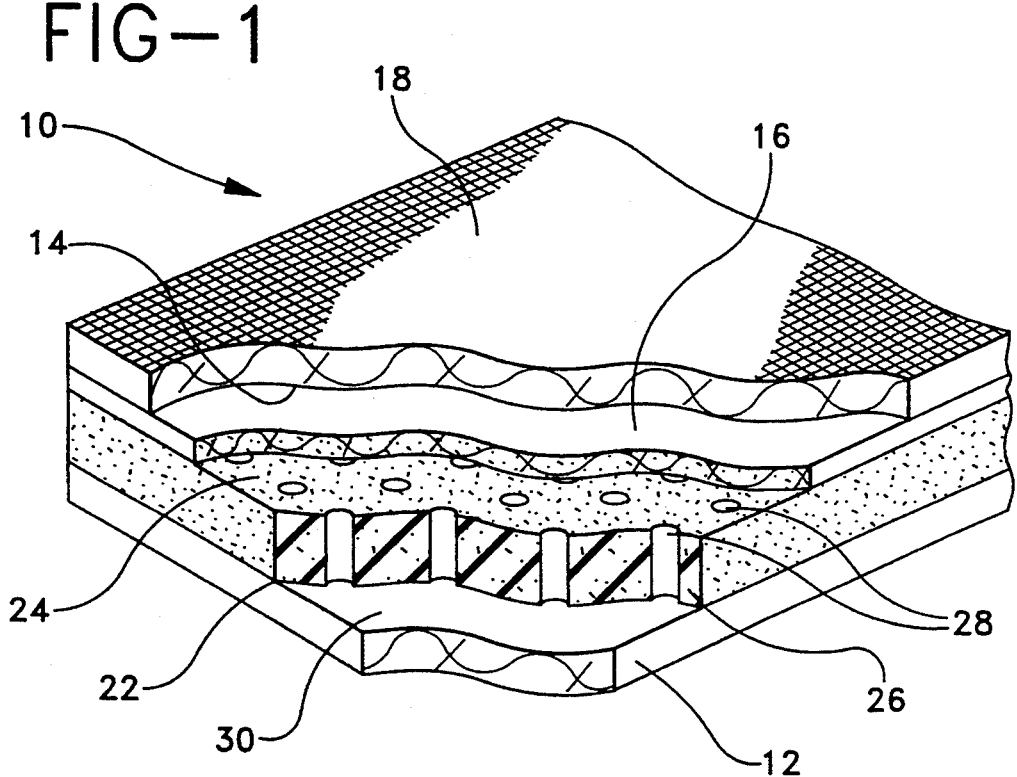
FIG. 1 is a perspective view of the multisegment composite material exposing the segments.

Adverting to FIG. 1, a multisection composite material 10 useful in forming compression braces for orthopedic support of a body part includes a user contacting fabric section 12 formed from substantially hydrophobic fibers which has multidimensional stretch properties. Composite 10 also includes an outermost fabric section 14 formed from bonding two dissimilar fabrics, a first fabric layer 16 formed from hydrophilic fibers having multidimensional stretch properties and a second fabric layer 18 formed from hydrophobic fibers. Composite 10 further includes an intermediate section 20 which has a first surface 22 and a second surface 24. Intermediate section 20 is formed from a closed cell foam 26 having a multiplicity of perforations 28 therethrough from first surface 22 to second surface 24. Intermediate section 20 has multidimensional elastic properties sufficient for providing compressive strain useful for support of a body part. Intermediate section 20 has first surface 22 bonded to a surface 30 of user contacting section 12 and second surface 24 bonded to first fabric layer 16. Intermediate section first surface 22 may be bonded to surface 30 of the user contacting section and intermediate section second surface 24 may be bonded to first fabric layer 16 by a suitable adhesive, water based, solvent based or hot melt, by ultrasonic welding, solvent welding or any other technique well known in the art of bonding fabric to foam. Preferably intermediate section first surface 22 is bonded to surface 30 and intermediate section second surface 24 is bonded to first fabric layer 16 by a solvent based adhesive.

Suitable hydrophobic fibers for forming user contacting section 12 include, but are not limited to nylon, polyester, polypropylene, blends of nylon, polyester and polypropylene and the like. Suitable fabrics for user contacting section 12 may be formed by weaving, knitting, and nonwoven techniques such as spun bonding, air laying and the like. A preferred fabric for user contacting section 12 is circular knit nylon formed from sixty to eighty denier, twenty to thirty filament nylon yarn.

Intermediate section 20 may be formed from closed cell foams such as polyurethane, natural rubber, polychloroprene and the like. A preferred foam is polychloroprene such as that made by foaming dupont Neoprene GW TM (E. I. duPont, Wilm. DE) to a density between about 0.15 to about 0.20 grams per cubic centimeter. Foams may be formed from polymer chips by several methods. Any of the standard methods for expanding or blowing and curing the substantially solid polychloroprene chips into a stable closed cell foam may be used in the present invention. The foam is cut into sheets having a thickness between about 2.5 millimeters (mm) to about 4.0 mm.

The foam sheet then has the user contacting fabric segment and the outermost fabric segment bonded to the first and second surfaces respectively. Since, in the preferred embodiment, the user contacting fabric segment and the outermost fabric segment are preferably formed by a circular knit process that forms a tube, these fabric segments have a maximum stretch direction circumferentially and a minimum stretch direction longitudinally. The knit tube structure is then slit longitudinally to form a linear sheet having longitudinal minimum stretch direction and an orthogonal minimum stretch direction. Preferably, both the user contacting fabric segment and the outermost fabric segment are bonded to the intermediate foam layer with the maximum stretch direction aligned. The bonding of these directionally aligned fabric segments to the foam thus provides a directionality or "grain" to the composite material produced. Preferably, the composite material of the present invention has a tensile strength in the width or maximum stretch direction of between about 15 to about 35 kilograms/square centimeter (kg/cm$^2$) at between about 200 to about 500 percent elongation and an ultimate tensile strength in the length or minimum stretch direction between about 25 to about 45 kg/cm$^2$ at between 150 to about 350 percent elongation. The composite material of the present invention having the preferred density and strength properties, will, when formed into a brace which is correctly sized for the user's physical stature, provide a compressive strain to a body part in the range of about 20 to about 80 mm of mercury (mm Hg) per square centimeter that is suitable for providing orthopedic support to the body part.

The multiplicity of perforations 28 in the foam may occupy any amount of the volume of the foam that does not substantially reduce the density of the foam, hence its ability to provide compressive support. Preferably, perforations 28 occupy between about three to about ten percent of the volume of the foam and, given the ranges of the tensile strength and elongation values for the preferred composite material with the polychloroprene foam, do not adversely effect the foam's ability to provide the required compressive stress.

Figure 2:
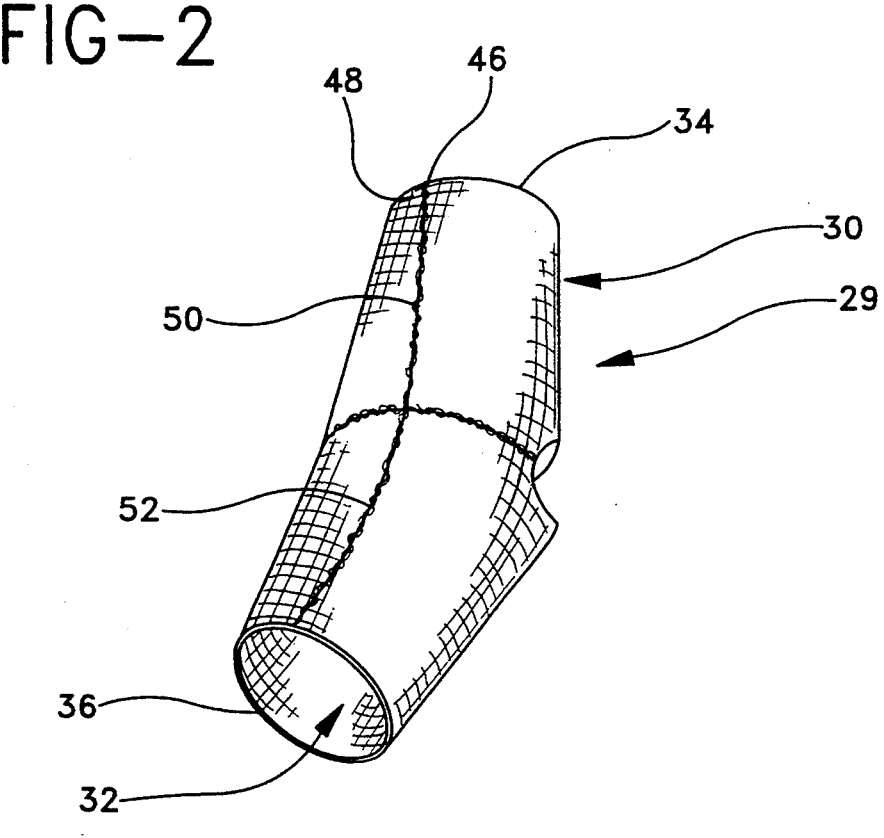
FIG. 2 is a perspective view of an ankle brace of the present invention.
Figure 3:
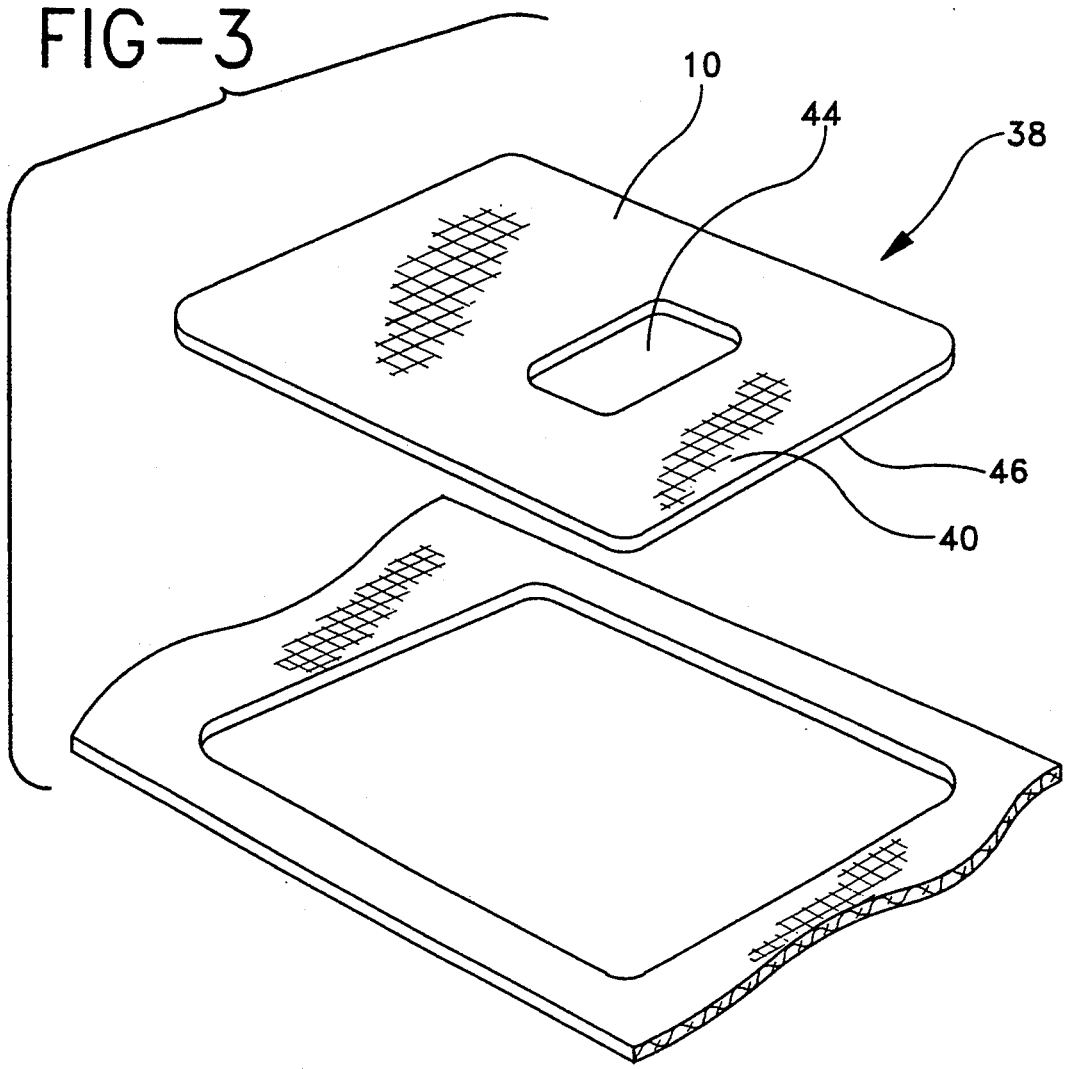
FIG. 3 is an exploded perspective view of a sheet of the multisection composite material of the present invention with a design for an ankle brace cut therefrom.

Adverting to FIGS. 2–6, a compression brace of the present invention for a body part as illustrated in FIG. 2 for an ankle. An ankle brace 29 includes a substantially tubular structure 30 which has a passageway 32 therethrough open from a first end 34 to a second end 36. Tubular structure 30 is formed from a sheet 38 of composite 10 as is shown in FIG. 3. For the case shown in FIG. 2 when structure 30 is intended as an ankle brace, sheet 38 is cut to a shape 40 having a design 42 with an opening 44 for the heel portion of a foot and edges 46 and 48. Cut shape 40 is formed into tubular structure 30 by joining edges 46 and 48. Edges 46 and 48 may be joined by adhesive bonding, ultrasonic welding, heat compression, solvent bonding, sewing, mechanical fastening and the like. A preferred embodiment of the ankle brace, as is shown in FIG. 2, has a seam 50 formed as a butt joint 52 joined by sewing.

A brace may be produced from the shape cut to the design as a single piece of composite material of the invention to form the substantially tubular structure. Alternatively, the brace may be constructed of a plurality of pieces of the material of the invention joined at edges to form the substantially tubular structure. Preferably, both where the brace is constructed from a single piece or plurality of pieces, account is taken of the differential stretch properties between the maximum stretch and minimum stretch directions of the composite material of the invention. As the design is laid out to form the shape for cutting, the placement of the design on the sheet may be set to favor the maximum stretch, minimum stretch direction or somewhere between the maximum and minimum stretch directions depending on where the particular shape will be used in forming the substantially tubular structure and the contour of the body part to be covered. This utilization of the differential stretch properties enables formation of a compression brace with control of the placement of compressive stress about the body part supported by allowing differential stretch between one area of the brace and another.

The recognition that proper alignment of differential stretch in the layout of the design controls the placement of the compression in a brace of the present invention allows substantial elimination of areas within an individual brace where too little compression or too much compression is applied to a correctly sized body part and permits maintenance of substantial uniformity of applied compression in all units of a brace of a particular size for a particular application.

Figure 4:
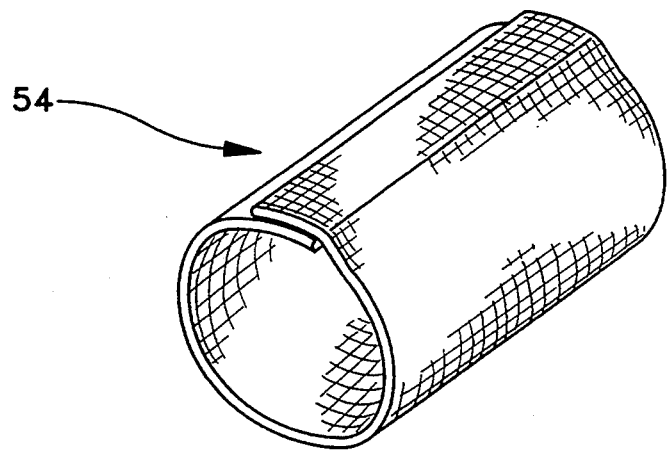
FIG. 4 is a perspective view of a wrist brace of the present invention.
Figure 5:
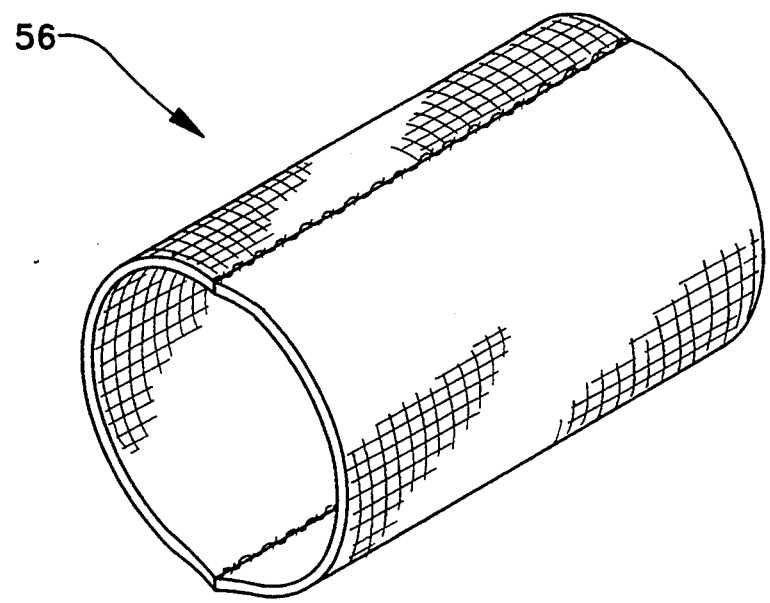
FIG. 5 is a perspective view of a thigh brace of the present invention.
Figure 6:
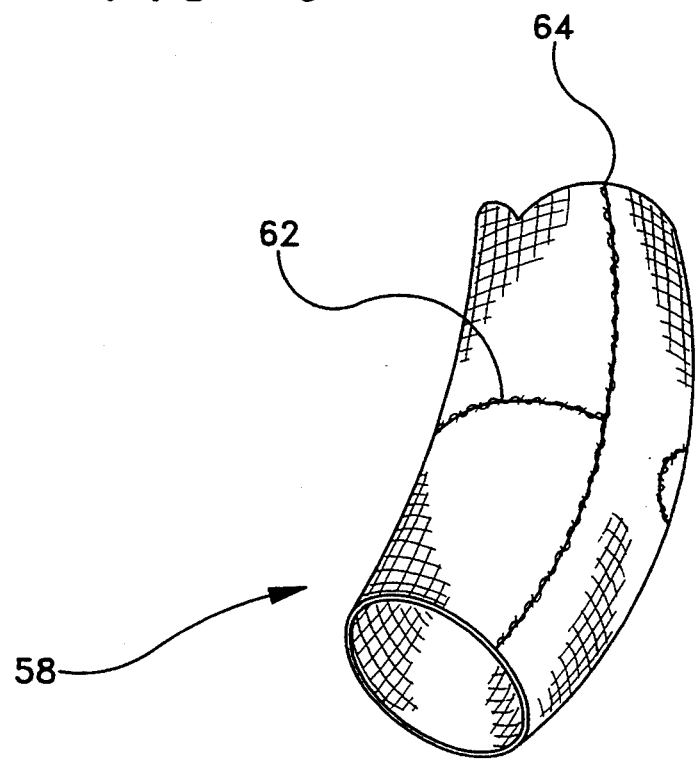
FIG. 6 is a perspective view of an elbow brace of the present invention.
Figure 7:
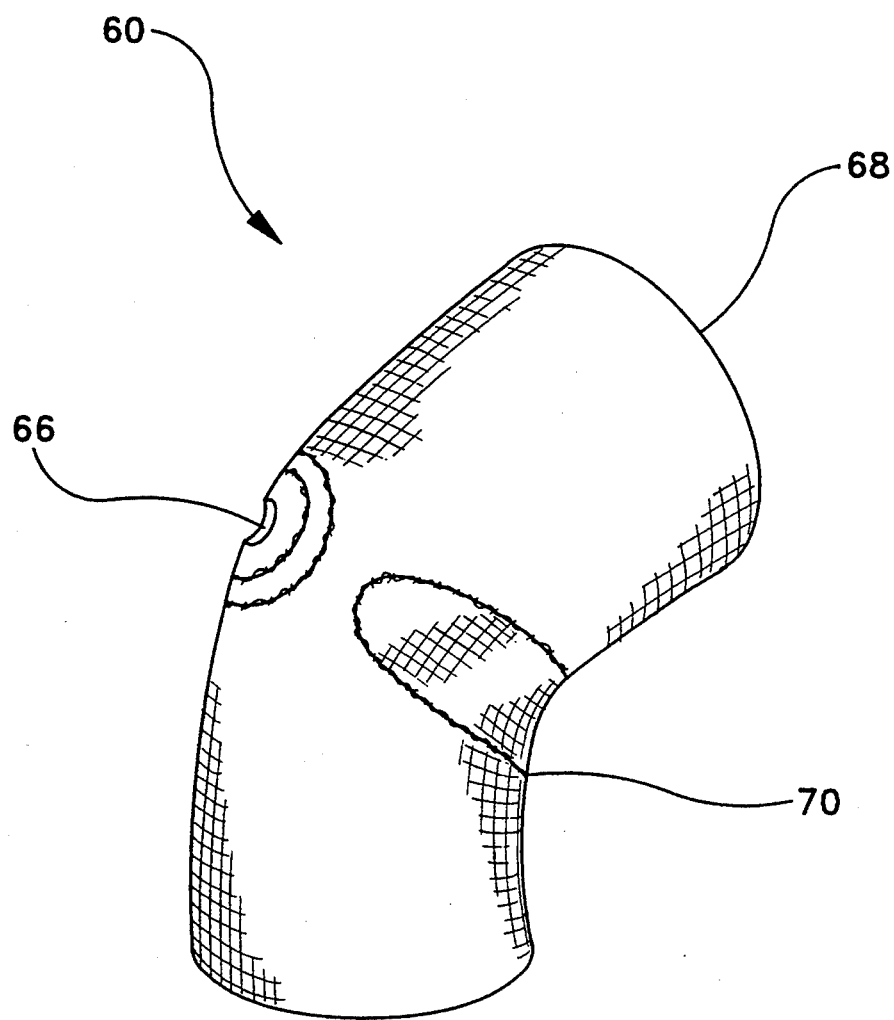
FIG. 7 is perspective view of a knee brace of the present invention.

Using FIGS. 2 and 3 showing the compression brace for the ankle as a model, a similar alternate embodiment of a brace 54 for the wrist is shown in FIG. 4, a brace 56 for the thigh is shown in FIG. 5, a brace 58 for the elbow is shown in FIG. 6 and a brace 60 for the knee is shown in FIG. 7. In each of these cases, the substantially tubular brace structure is formed in the manner illustrated by FIG. 3 wherein sheet 38 is cut to shape 40 having design 42 appropriate for ankle brace 29. For the embodiments in FIGS. 4–7, specific designs are developed to conform to and accommodate the contours of the portion of the body to which it is to be applied. Additionally, the brace may include a seam or seams to provide specific shapes. A preferred embodiment of a brace of the present invention is formed from more than one piece of the composite material of the present invention allowing optimal utilization of differential stretch properties of the pieces to maintain substantially uniform compression about the supported body part. As illustrated in FIG. 6, Brace 58 has seams 62 and 64 to provide the design shaped for the elbow. Further, as can be noted in FIG. 7, compression brace 60 for the knee may include an opening 66 to expose at least a portion of the patella and seams 68 and 70 to provide the design shaped for the knee. The designs are further refined to include small, medium, large and extra-large sizes for accommodation of users having different physical stature.

Table I below shows the size ranges as the circumference in centimeters at the measurement location for each brace.

TABLE I

| Brace/Measurement location | Size (Centimeters) | | | |
| --- | --- | --- | --- | --- |
| | Small | Medium | Large | Extra-large |
| Elbow/Mid Elbow | 22.8–25.4 | 25.5–28.6 | 28.7–31.8 | 31.9–37.4 |
| Thigh/Mid-Thigh | 48.2–50.8 | 50.9–55.9 | 56.0–63.5 | 63.6–71.1 |
| Knee/Mid-Knee | 30.4–36.2 | 36.3–42.5 | 42.6–48.9 | 49.0–55.2 |
| Ankle/Just above Ankle bone | 17.8–20.3 | 20.4–23.5 | 23.6–26.7 | 26.8–30.5 |

The wrist brace 54 is preferably provided as a single size with provisions for an adjustable closure, preferably the closure is a multiple hooks and eyes fastener. The provision of several sizes of each brace provides for a range of available braces with substantially similar compressive stress for users having different physical stature, while the utilization of the differential stretch of the composite material of the present invention in the layout of the design substantially ensures that each unit of a brace of a particular size for a particular application will have substantially similar compression profiles.

A method of the present invention for making orthopedic support braces from the composite material of the present invention having a substantially uniform support profile for an individual brace and for substantially all of a production lot of braces includes selecting a series of size ranges suitable for a particular application. A design is developed for cutting a shape or shapes, which when joined together at edges form a substantially tubular structure for supporting a body part. As part of the design process, the direction of the design which requires the maximum stretch is identified. The design is then placed on a sheet of the composite material of the present invention so that the identified direction of required maximum stretch is aligned with the direction of maximum stretch of the sheet. The sheet is then cut to the shape of the design and joined at the edges to form the substantially tubular brace structure. In manufacturing a production lot of braces of the present invention for a particular application, placement of the design on the composite sheet so that the direction of required maximum stretch for each unit of each shape to be cut is substantially aligned to the direction of maximum stretch for the sheet ensures substantial uniformity of the support profile for substantially all of the lot.

In a brace of the present invention, moisture emitted from the user's skin is passed through the hydrophobic user contacting layer to the intermediate foam layer, whereupon it may pass through the multiplicity of perforations to the outermost layer. The outermost layer, by having a first hydrophilic layer bonded to the second surface of the foam, draws emitted moisture away from perforations 28 onto second surface 24 of intermediate foam layer 20 and spreads it for evaporation through the second hydrophobic fabric layer. By drawing the emitted moisture away from the perforations and spreading it, the rate of evaporation, which is dependent on the surface area of the water, is substantially increased and the rate of emitted moisture transport through the perforations is substantially enhanced. The hydrophobic first layer 16 further serves as a reservoir to prevent wet spots from developing around perforations 28 which preferably occupy only between about three to ten percent of the volume of foam 20 thus facilitating evaporation of emitted moisture from substantially all of the brace surface instead of only the area around the openings of the perforations. The drawing away of emitted moisture from the perforations with subsequent spreading of moisture across substantially the entire surface 24 of intermediate layer 20 provides for substantially increased evaporation of emitted water through the hydrophobic second fabric layer 18 serving as the outside surface of the brace. The enhanced moisture transport allows a user of a closed cell foam support brace of the present invention the benefits of the support provided by the closed cell foam with improved comfort.

What is claimed is:

1. A multisection composite material useful in forming compression braces for orthopedic support of a body part comprising:

a user contacting fabric section formed from substantially hydrophobic fibers and having multidimensional stretch properties, said user contacting fabric being a longitudinally slit circular knit fabric having a minimum stretch in a longitudinal direction and an orthogonal maximum stretch direction said fiber being selected from the group consisting of nylon, polyester, polypropylene and blends thereof;

an intermediate section having a first surface and a second surface, said intermediate section formed from a closed cell foam having a multiplicity of perforations therethrough from said first surface to said second surface, said intermediate section having multidimensional elastic properties sufficient for providing compressive strain useful for support of the body part, said intermediate section first surface being bonded to a surface of said user contacting section and said second surface being bonded to said first fabric layer of said outermost section; and an outermost fabric section being a two layer longitudinally slit circular knit fabric formed from bonding two dissimilar fabrics comprising a first fabric layer having multidimensional stretch properties formed from hydrophilic fiber selected from the group consisting of cotton, wool, silk, viscose rayon and blends thereof, and a second fabric layer having multidimensional stretch properties formed from hydrophobic fiber selected from the group consisting of polyester, nylon, acrylic, polypropylene and blends thereof, said first fabric layer and said second fabric layer being bonded together by linkage of overlapping yarns and fibers of said first layer and said second layer, said outermost fabric section having a longitudinal direction of minimum stretch and an orthogonal maximum stretch direction, said first layer being bonded to said second surface of said intermediate foam section so that said outermost section maximum stretch direction is aligned with said maximum stretch direction of said user contacting section, said second layer thereby serving as an outer surface of said multisection composite.

2. The material of claim 1 wherein said user contacting section and said outermost fabric section having said maximum stretch directions aligned, are bonded to said intermediate foam section by a solvent based adhesive, said material having an elongation in the minimum stretch direction between about one hundred fifty and about three hundred fifty percent and an elongation in the maximum stretch direction between about two hundred and about five hundred percent.

* * * * *